United States Patent
Craig

(10) Patent No.: US 9,677,094 B2
(45) Date of Patent: Jun. 13, 2017

(54) PROCESS OF PRODUCING A FERMENTATION PRODUCT

(75) Inventor: Joyce Craig, Pittsboro, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 13/983,949

(22) PCT Filed: Feb. 6, 2012

(86) PCT No.: PCT/US2012/023914
§ 371 (c)(1),
(2), (4) Date: Aug. 6, 2013

(87) PCT Pub. No.: WO2012/109119
PCT Pub. Date: Aug. 16, 2012

(65) Prior Publication Data
US 2013/0316407 A1 Nov. 28, 2013

Related U.S. Application Data

(60) Provisional application No. 61/439,957, filed on Feb. 7, 2011.

(51) Int. Cl.
| | |
|---|---|
| C12P 7/14 | (2006.01) |
| C12N 1/18 | (2006.01) |
| C12N 1/38 | (2006.01) |
| C12N 9/26 | (2006.01) |
| C12P 7/08 | (2006.01) |
| C12P 19/14 | (2006.01) |

(52) U.S. Cl.
CPC ............ *C12P 7/14* (2013.01); *C12N 1/18* (2013.01); *C12N 1/38* (2013.01); *C12N 9/2414* (2013.01); *C12P 7/08* (2013.01); *C12P 19/14* (2013.01)

(58) Field of Classification Search
CPC ........................................... C12P 7/14
See application file for complete search history.

(56) References Cited

U.S. PATENT DOCUMENTS

2009/0047382 A1* 2/2009 Cates et al. ................. 426/14

FOREIGN PATENT DOCUMENTS

| EP | 1916308 A1 | 4/2008 |
|---|---|---|
| WO | 2008049615 A1 | 5/2008 |

OTHER PUBLICATIONS

Corzo-Marinez et al, 2010, J Agric Food Chem 58(1), 500-506.
Metz et al, 2003, Arch Biochem Biophys 419(1), 41-49.
Sato et al, 1992, Appl Environ Microbiol 58(2), 734-736.
Voziyan et al, 2002, J Biol Chem 277(5), 3397-3403.
Voziyan et al, 2005, Cell Mol Life Sci 62(15), 1671-1681.
Voziyan et al, 2005, NY Acad Sci 1043, 807-816.

* cited by examiner

*Primary Examiner* — Paul Holland
(74) *Attorney, Agent, or Firm* — David A. Fazzolare

(57) ABSTRACT

The invention relates to a process of producing a fermentation product in the presence of pyridoxamine.

28 Claims, No Drawings

PROCESS OF PRODUCING A FERMENTATION PRODUCT

CROSS-REFERENCE TO RELATED APPLICATIONS

This application is a 35 U.S.C. 371 national application of PCT/US2012/023914 filed Feb. 6, 2012, which claims priority or the benefit under 35 U.S.C. 119 of U.S. provisional application No. 61/439,957 filed Feb. 7, 2011, the contents of which are fully incorporated herein by reference.

FIELD OF THE INVENTION

The present invention relates to methods of producing a fermentation product from a starch-containing material.

BACKGROUND ART

A vast number of commercial products that are difficult to produce synthetically are today produced by fermenting organisms. Such products include alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones. Fermentation is also commonly used in the consumable alcohol (e.g., beer and wine), dairy (e.g., in the production of yogurt and cheese), leather, and tobacco industries.

A vast number of processes of producing fermentation products, such as ethanol, by fermentation of sugars provided by degradation of starch-containing material are known in the art.

However, production of fermentation products, such as ethanol, from such plant materials is still too costly. Therefore, there is a need for providing processes that can increase the yield of the fermentation product and thereby reducing the production costs.

WO 2008/049615 discloses the use of vitamins in a fermentation process for the production of, e.g., amino acids or ethanol, wherein at least 4 vitamins selected from the group consisting of: thiamine, cobalamine, riboflavine, niacinamide, pantothenic acid, biotin, ascorbic acid, retinol, procalciol, tocopherol, folic acid and pyridoxamine are used, and wherein the use of these vitamins enhances the bacterial growth rate at least by 50 percent and the product concentration at least by 10 percent compared to a reference fermentation process, performed without adding vitamins.

Corzo-Marinez et al. (*J. Agric. Food. Chem.* 58(1):500-6 (2010)) disclose that pyridoxamine has an inhibitory effect of on the initial stages of the Maillard reaction during the formation of conjugates of beta-lactoglobulin with galactose and tagatose.

Voziyan et al. (*Cell Mol. Life. Sci.* 62(15): 1671-1681 (2005)) disclose that pyridoxamine can inhibit glycation reactions and the formation of advanced glycation end products (AGEs). The mechanism of action of pyridoxamine includes inhibition of AGE formation by blocking oxidative degradation of the Amadori intermediate of the Maillard reaction.

Metz et al. (*Arch. Biochem. Biophys.* 419(1): 41-49 (2003)) disclose that pyridoxamine inhibits the formation of advanced lipoxidation end-products on protein during lipid peroxidation reactions, and has a strong lipid-lowering effect in streptozotocin-induced diabetic and Zucker obese rats, and protects against the development of nephropathy in both animal models.

Voziyan et al. (*NY Acad. Sci.* 1043: 807-816 (2005)) disclose that pyridoxamine is a critical transient intermediate in catalysis of transamination reactions by vitamin B6-dependent enzymes.

Sato et al. (*Appl. Environ. Microbiol.* 58(2): 734-736 (1992)) disclose that the addition of yeast extract, a vitamin mixture containing vitamin B(12), biotin, pyridoxamine, and p-aminobenzoic acid enhanced formation of ethanol but decreased lactate production in the fermentation of cellulose by *Clostridium thermocellum*.

It is an object of the present invention to provide an improved process for producing a fermentation product.

SUMMARY OF THE INVENTION

The present invention relates to a process of producing a fermentation product from a gelatinized starch-containing material. In particular, the present invention relates to a process of producing a fermentation product, comprising:

(a) liquefying a starch-containing material to a dextrin with an alpha-amylase in the presence of pyridoxamine;

(b) saccharifying the dextrin to a sugar with a glucoamylase; and (c) fermenting the sugar using a fermenting organism.

The present invention also relates to a process of producing a fermentation product, comprising:

(a) liquefying a starch-containing material to a dextrin with an alpha-amylase in the presence of pyridoxamine;

(b) saccharifying the dextrin to a sugar with a saccharifying enzyme; and (c) fermenting the sugar using a fermenting organism.

In another embodiment, the present invention relates to a process of producing a fermentation product, comprising:

(a) treating a starch-containing material with an alpha-amylase in the presence of pyridoxamine;

(b) liquefying the treated starch-containing material to a dextrin with an alpha-amylase;

(c) saccharifying the dextrin to a sugar with a saccharifying enzyme; and (d) fermenting the sugar using a fermenting organism to produce the fermentation product.

In another embodiment, the present invention relates to a process of producing a sugar, comprising:

(a) liquefying a starch-containing material to a dextrin with an alpha-amylase in the presence of pyridoxamine; and (b) saccharifying the dextrin to a sugar with a saccharifying enzyme.

In another embodiment, the present invention relates to a process of producing a sugar, comprising:

(a) treating a starch-containing material with an alpha-amylase in the presence of pyridoxamine;

(b) liquefying the treated starch-containing material to a dextrin with an alpha-amylase; and (c) saccharifying the dextrin to a sugar with a saccharifying enzyme.

The present invention also relates to a process of producing a dextrin, comprising liquefying a starch-containing material to the dextrin with an alpha-amylase in the presence of pyridoxamine.

In another embodiment, the present invention relates to process of producing a dextrin, comprising:

(a) treating a starch-containing material with an alpha-amylase in the presence of pyridoxamine; and (b) liquefying the treated starch-containing material to a dextrin with an alpha-amylase.

DETAILED DESCRIPTION OF THE INVENTION

Processes for Producing Fermentation Products, Dextrins, and Sugars from Starch-Containing Materials The present invention relates to a process of producing a fermentation product from a gelatinized starch-containing material. In particular, the present invention relates to a process of producing a fermentation product, comprising:

(a) liquefying a starch-containing material to a dextrin with an alpha-amylase in the presence of pyridoxamine;

(b) saccharifying the dextrin to a sugar with a glucoamylase; and (c) fermenting the sugar using a fermenting organism.

The present invention also relates to a process of producing a fermentation product, comprising:

(a) liquefying a starch-containing material to a dextrin with an alpha-amylase in the presence of pyridoxamine;

(b) saccharifying the dextrin to a sugar with a saccharifying enzyme; and (c) fermenting the sugar using a fermenting organism.

In another embodiment, the present invention relates to a process of producing a fermentation product, comprising:

(a) treating a starch-containing material with an alpha-amylase in the presence of pyridoxamine;

(b) liquefying the treated starch-containing material to a dextrin with an alpha-amylase;

(c) saccharifying the dextrin to a sugar with a saccharifying enzyme; and (d) fermenting the sugar using a fermenting organism to produce the fermentation product.

In another embodiment, the present invention relates to a process of producing a sugar, comprising:

(a) liquefying a starch-containing material to a dextrin with an alpha-amylase in the presence of pyridoxamine; and (b) saccharifying the dextrin to a sugar with a saccharifying enzyme.

In another embodiment, the present invention relates to a process of producing a sugar, comprising:

(a) treating a starch-containing material with an alpha-amylase in the presence of pyridoxamine;

(b) liquefying the treated starch-containing material to a dextrin with an alpha-amylase; and (c) saccharifying the dextrin to a sugar with a saccharifying enzyme.

The present invention also relates to a process of producing a dextrin, comprising liquefying a starch-containing material to the dextrin with an alpha-amylase in the presence of pyridoxamine.

In another embodiment, the present invention relates to a process of producing a dextrin, comprising:

(a) treating a starch-containing material with an alpha-amylase in the presence of pyridoxamine; and (b) liquefying the treated starch-containing material to a dextrin with an alpha-amylase.

In an embodiment, the pyridoxamine is present in an amount of 1-100 micrograms/g dry solids, e.g., 5-50, 10-40, 10-25 micrograms/g dry solids.

Starch is formed within plant cells as tiny granules insoluble in water. When put in cold water, the starch granules may absorb a small amount of the liquid and swell. At temperatures up to 50° C. to 75° C. the swelling may be reversible. However, with higher temperatures an irreversible swelling called "gelatinization" begins.

Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. Two processes are preferred according to the invention: wet and dry milling. In dry milling whole kernels are milled and used. Wet milling gives a good separation of germ and meal (starch granules and protein) and is often applied at locations where the starch hydrolyzate is used in the production of, e.g., syrups. Both dry and wet milling are well known in the art of starch processing and may be used in a process of the invention. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

After the particle size of the starch-containing material is reduced, a slurry comprising the starch-containing material and water is formed. The aqueous slurry may contain from 10-55 wt. % dry solids (DS), preferably 25-45 wt. % dry solids (DS), more preferably 30-40 wt. % dry solids (DS) of starch-containing material.

The starch-containing material may be used to produce a sugar, a dextrin, or a fermentation product. Generally, the starch-containing material is liquefied to a dextrin with an alpha-amylase, which is then followed by saccharification (a process which converts the dextrin to a sugar) and fermentation (a process which converts the sugar to a fermentation product).

Treatment Prior to Liquefaction

In an embodiment, the starch-containing material is treated with an alpha-amylase prior to liquefaction in the presence of pyridoxamine. This treatment may be carried out at any pH and temperature suitable for enzyme activity for a period of time to allow for the enzymatic reaction to take place. In an embodiment, the temperature is in the range of 20-75° C., e.g., 20-65° C. or 40-60° C.; the pH is in the range of 4.5-6.5; and the period of time is in the range of 5 minutes-2 hours, e.g., 5 minutes-1 hour.

Liquefaction

The liquefaction is carried out in the presence of an alpha-amylase, preferably a bacterial alpha-amylase and/or acid fungal alpha-amylase. In an embodiment, a pullulanase, isoamylase, and/or phytase is/are added during liquefaction.

The dextrin may be recovered by methods well known in the art.

During a typical liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 77-86° C., 80-85° C., or 83-85° C.) and an alpha-amylase(s) is (are) added to initiate liquefaction (thinning). The liquefaction process is carried out at 85° C. for 1-2 hours. The pH is generally between 5.5 and 6.2. In order to ensure optimal enzyme stability under these conditions, 1 mM of calcium is optionally added (to provide about 40 ppm free calcium ions). After such treatment, the liquefied starch will have a "dextrose equivalent" (DE) of 10-15.

The slurry may be subsequently jet-cooked at between 95-140° C., e.g., 105-125° C., for about 1-15 minutes, e.g., about 3-10 minutes, especially around 5 minutes. The slurry is then cooled to 60-95° C. and more alpha-amylase(s) is(are) added to obtain the final hydrolysis (secondary liquefaction). The jet-cooking process is carried out at pH 4.5-6.5, typically at a pH between 5 and 6. The alpha-amylase may be added as a single dose, e.g., before jet cooking.

Liquefaction may be carried out as a three-step hot slurry process. The slurry is heated to between 60-95° C., e.g., 80-85° C., and an alpha-amylase is added to initiate liquefaction (thinning). Then the slurry may be jet-cooked at a temperature between 95-140° C., e.g., 105-125° C., for about 1-15 minutes, e.g., about 3-10 minutes, especially around 5 minutes. The slurry is cooled to 60-95° C. and more alpha-amylase is added to finalize the hydrolysis (secondary liquefaction). The liquefaction process is usually carried out at a pH of 4.5-6.5, in particular at a pH from 5 to 6. All of the alpha-amylases may be added as a single dose, e.g., before jet cooking.

Saccharification

Saccharification may be carried out using conditions well known in the art with a saccharifying enzyme, e.g., beta-amylase, glucoamylase or maltogenic amylase, and optionally a debranching enzyme, such as an isoamylase or a pullulanase. For instance, a full saccharification step may last from about 24 to about 72 hours, however, it is also common to do a pre-saccharification of typically 40-90 minutes at a temperature between 30-65° C., typically about 60° C., followed by complete saccharification before initiation of fermentation. Saccharification is typically carried out at a temperature in the range of 20-75° C., e.g., 25-65° C. and 40-70° C., typically around 60° C., and at a pH between about 4 and 5, normally at about pH 4.5.

In an embodiment, saccharification results in the production of maltose.

In another embodiment, saccharification results in the production of glucose.

The glucose may be converted to fructose.

The sugars may be recovered by methods well known in the art.

Simultaneous Saccharification and Fermentation (SSF)

The saccharification and fermentation steps may be carried out simultaneously. In this embodiment, there is no holding stage for the saccharification, meaning that a fermenting organism, such as yeast, and enzyme(s) are added together. SSF is typically carried out at conditions (e.g., temperature and/or pH) suitable, preferably optimal, for the fermenting organism(s) in question, e.g., a temperature of 20-40° C., e.g., 26-34° C., preferably around 32° C., when the fermentation organism is yeast, such as a strain of *Saccharomyces cerevisiae*, and the fermentation product is ethanol.

Other fermentation products may be fermented at conditions and temperatures, well known to persons skilled in the art, suitable for the fermenting organism in question. According to the invention the temperature may be adjusted up or down during fermentation.

Fermentation

Different kinds of fermenting organisms may be used for fermenting sugars derived from starch-containing material. Fermentations are conventionally carried out using yeast, such as *Saccharomyces cerevisae*, as the fermenting organism. However, bacteria and filamentous fungi may also be used as fermenting organisms. Some bacteria have higher a fermentation temperature optimum than, e.g., *Saccharomyces cerevisae*. Therefore, fermentations may in such cases be carried out at temperatures as high as 75° C., e.g., between 40-70° C., such as between 50-60° C. However, bacteria with a significantly lower temperature optimum down to around room temperature (around 20° C.) are also known.

For ethanol production using yeast, the fermentation may be performed for 24 to 96 hours, in particular for 35 to 60 hours. In an embodiment the fermentation is carried out at a temperature between 20 to 40° C., preferably 26 to 34° C., in particular around 32° C. The temperature may be adjusted up or down during fermentation. In an embodiment the pH is from pH 3 to 7, e.g., 3.5 to 6, 4 to 5, and around 5.

Other fermentation products may be fermented at temperatures known to the skilled person in the art to be suitable for the fermenting organism in question.

The fermentation conditions are determined based on, e.g., the kind of plant material, the available fermentable sugars, the fermenting organism(s) and/or the desired fermentation product. One skilled in the art can easily determine suitable fermentation conditions. The fermentation may according to the invention be carried out at conventionally used conditions. Preferred fermentation processes are anaerobic processes.

The methods or processes of the invention may be performed as a batch or as a continuous process. Fermentations of the invention may be conducted in an ultrafiltration system wherein the retentate is held under recirculation in the presence of solids, water, and the fermenting organism, and wherein the permeate is the desired fermentation product containing liquid. Equally contemplated are methods/ processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s), and may include the fermenting organism(s).

The fermentation medium may comprise nutrients and growth stimulator(s) for the fermenting organism(s). Nutrient and growth stimulators are widely used in the art of fermentation and include nitrogen sources, such as ammonia; vitamins and minerals, or combinations thereof.

Following fermentation, the fermentation media or fermentation medium may further comprise the fermentation product.

Fermenting Organisms

The term "fermenting organism" refers to any organism, including bacterial and fungal organisms, including yeast and filamentous fungi, suitable for producing a desired fermentation product. Suitable fermenting organisms according to the invention are able to ferment, i.e., convert fermentable sugars, such as glucose, fructose, maltose, xylose, mannose or arabinose, directly or indirectly into the desired fermentation product.

Examples of fermenting organisms include fungal organisms such as yeast. Preferred yeast includes strains of the genus *Saccharomyces*, in particular strains of *Saccharomyces cerevisiae* or *Saccharomyces uvarum*; a strain of *Pichia*, preferably *Pichia stipitis* such as *Pichia stipitis* CBS 5773 or *Pichia pastoris*; a strain of the genus *Candida*, in particular a strain of *Candida utilis, Candida arabinofermentans, Candida diddensii, Candida sonorensis, Candida shehatae, Candida tropicalis*, or *Candida boidinii*. Other fermenting organisms include strains of *Hansenula*, in particular *Hansenula polymorpha* or *Hansenula anomala; Kluyveromyces*, in particular *Kluyveromyces fragilis* or *Kluyveromyces marxianus*; and *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes* and strains of *Thermoanaerobacter*, in particular *Thermoanaerobacter* BG1 L1 (*Appl. Microbiol. Biotech.* 77: 61-86) and *Thermoanarobacter ethanolicus, Thermoanaerobacter thermosaccharolyticum*, or *Thermoanaerobacter mathranii*. Strains of *Lactobacillus* are also envisioned as are strains of *Corynebacterium glutamicum* R, *Bacillus thermoglucosidaisus*, and *Geobacillus thermoglucosidasius*.

In an embodiment the fermenting organism is a C6 sugar fermenting organism, such as a strain of, e.g., *Saccharomyces cerevisiae*.

In one embodiment the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

Commercially available yeast includes, e.g., RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

According to the invention the fermenting organism capable of producing a desired fermentation product from fermentable sugars, including glucose, fructose, maltose, xylose, mannose, or arabinose, is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation Products

The term "fermentation product" means a product produced by a method or process including fermenting using a fermenting organism. Fermentation products contemplated according to the invention include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. Preferred fermentation processes used include alcohol fermentation processes. The fermentation product, such as ethanol, obtained according to the invention, may preferably be used as fuel. However, in the case of ethanol it may also be used as potable ethanol.

Recovery

Subsequent to fermentation, the fermentation product may be separated from the fermentation medium by methods well known in the art, e.g., by distillation.

In particular, the fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

Starch-Containing Materials

Any suitable starch-containing starting material, including granular starch (raw uncooked starch), may be used according to the present invention. The starting material is generally selected based on the desired fermentation product. Examples of starch-containing starting materials, suitable for use in methods or processes of the present invention, include barley, beans, cassaya, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley.

Enzymes

Even if not specifically mentioned in context of a method or process of the invention, it is to be understood that enzyme(s) is(are) used in an "effective amount".

Alpha-Amylases

According to the invention any alpha-amylase may be used, such as of fungal, bacterial or plant origin. In a preferred embodiment the alpha-amylase is an acid alpha-amylase, e.g., acid fungal alpha-amylase or acid bacterial alpha-amylase. The term "acid alpha-amylase" means an alpha-amylase (E.C. 3.2.1.1) which added in an effective amount has activity optimum at a pH in the range of 3 to 7, preferably from 3.5 to 6, or more preferably from 4-5.

Bacterial Alpha-Amylases

According to the invention a bacterial alpha-amylase is preferably derived from the genus *Bacillus*.

In a preferred embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp. Specific examples of contemplated alpha-amylases include the *Bacillus amyloliquefaciens* alpha-amylase SEQ ID NO: 5 in WO 99/19467, the *Bacillus licheniformis* alpha-amylase shown in SEQ ID NO: 4 in WO 99/19467, and the *Bacillus stearothermophilus* alpha-amylase shown in SEQ ID NO: 3 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

The *Bacillus* alpha-amylase may also be a variant and/or hybrid, especially one described in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, and 6,297,038 (hereby incorporated by reference) and include *Bacillus stearothermophilus* alpha-amylase (BSG alpha-amylase) variants having a deletion of one or two amino acids at positions R179 to G182, preferably a double deletion disclosed in WO 96/23873—see, e.g., page 20, lines 1-10 (hereby incorporated by reference), preferably corresponding to delta(181-182) compared to the amino acid sequence of *Bacillus stearothermophilus* alpha-amylase set forth in SEQ ID NO:3 disclosed in WO 99/19467 or the deletion of amino acids R179 and G180 using SEQ ID NO:3 in WO 99/19467 for numbering (which reference is hereby incorporated by reference). Even more preferred are *Bacillus* alpha-amylases, especially *Bacillus stearothermophilus* alpha-amylases, which have a double deletion corresponding to delta(181-182) and further comprise a N193F substitution (also denoted I181*+G182*+N193F) compared to the wild-type BSG alpha-amylase amino acid sequence set forth in SEQ ID NO:3 disclosed in WO 99/19467.

Bacterial Hybrid Alpha-Amylases

A hybrid alpha-amylase specifically contemplated comprises 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylase backbones): H154Y, A181T, N190F, A209V and Q264S and/or the deletion of two residues between positions 176 and 179, preferably the deletion of E178 and G179 (using SEQ ID NO: 5 WO 99/19467 for position numbering).

In an embodiment the bacterial alpha-amylase is dosed in an amount of 0.0005-5 KNU per g DS (dry solids), preferably 0.001-1 KNU per g DS, such as around 0.050 KNU per g DS.

Fungal Alpha-Amylases

Fungal alpha-amylases include alpha-amylases derived from a strain of the genus *Aspergillus*, such as, *Aspergillus kawachii, Aspergillus niger* and *Aspergillus oryzae* alpha-amylases.

A preferred acidic fungal alpha-amylase is an alpha-amylase which exhibits a high identity, i.e., at least 70%, at least 75%, at least 80%, at least 85%, at least 90%, at least 95%, at least 96%, at least 97%, at least 98%, at least 99% or even 100% identity to the mature part of the amino acid sequence shown in SEQ ID NO: 10 in WO 96/23874.

Another preferred acid alpha-amylase is derived from a strain *Aspergillus niger*. In a preferred embodiment the acid fungal alpha-amylase is the one from *Aspergillus niger* disclosed as "AMYA_ASPNG" in the Swiss-prot/TeEMBL database under the primary accession no. P56271 and described in WO 89/01969 (Example 3-incorporated by reference). A commercially available acid fungal alpha-amylase derived from *Aspergillus niger* is SP288 (available from Novozymes A/S, Denmark).

Other contemplated wild-type alpha-amylases include those derived from a strain of *Meripilus* and *Rhizomucor*, preferably a strain of *Meripilus giganteus* or *Rhizomucor pusillus* (WO 2004/055178 incorporated by reference).

In a preferred embodiment the alpha-amylase is derived from *Aspergillus* kawachii and disclosed by Kaneko et al., 1996, *J. Ferment. Bioeng.* 81: 292-298, "Molecular-cloning and determination of the nucleotide-sequence of a gene encoding an acid-stable alpha-amylase from *Aspergillus kawachii*"; and further as EMBL: #AB008370.

The fungal alpha-amylase may also be a wild-type enzyme comprising a starch-binding domain (SBD) and an alpha-amylase catalytic domain (i.e., non-hybrid), or a variant thereof. In an embodiment the wild-type alpha-amylase is derived from a strain of *Aspergillus kawachii*.

Fungal Hybrid Alpha-Amylases

In a preferred embodiment the fungal acid alpha-amylase is a hybrid alpha-amylase. Examples of fungal hybrid alpha-amylases include the ones disclosed in WO 2005/003311, U.S. Patent Application Publication No. 2005/0054071 (Novozymes), and WO 2006/069290 (Novozymes), which are hereby incorporated by reference. A hybrid alpha-amylase may comprise an alpha-amylase catalytic domain (CD) and a carbohydrate-binding domain/module (CBM), such as a starch binding domain, and optionally a linker.

Specific examples of hybrid alpha-amylases include those disclosed in Tables 1 to 5 of the examples in WO 2006/069290 including Fungamyl variant with the catalytic domain JA118 and *Athelia rolfsii* SBD (SEQ ID NO:100 in U.S. provisional application No. 60/638,614), *Rhizomucor pusillus* alpha-amylase with *Athelia rolfsii* AMG linker and SBD (SEQ ID NO:101 in U.S. provisional application No. 60/638,614), *Rhizomucor pusillus* alpha-amylase with *Aspergillus niger* glucoamylase linker and SBD (which is disclosed in Table 5 as a combination of amino acid sequences SEQ ID NO:20, SEQ ID NO:72 and SEQ ID NO:96 in U.S. application Ser. No. 11/316,535) or as V039 in Table 5 in WO 2006/069290, and *Meripilus giganteus* alpha-amylase with *Athelia rolfsii* glucoamylase linker and SBD (SEQ ID NO:102 in WO 2006/069290). Other hybrid alpha-amylases are listed in Tables 3, 4, 5, and 6 in Example 4 in U.S. application Ser. No. 11/316,535 and WO 2006/069290 (which are hereby incorporated by reference).

Other specific examples of hybrid alpha-amylases include those disclosed in U.S. Patent Application Publication No. 2005/0054071, including those disclosed in Table 3 on page 15, such as *Aspergillus niger* alpha-amylase with *Aspergillus kawachii* linker and starch binding domain.

Other alpha-amylases exhibit a high degree of sequence identity to any of above mentioned alpha-amylases, i.e., at least 70%, at least 75%, at least 80%, at least 85%, at least 90%, at least 95%, at least 96%, at least 97%, at least 98%, at least 99% or even 100% identity to the mature enzyme sequences disclosed above.

An acid alpha-amylase may according to the invention be added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

Commercial Alpha-Amylase Products

Preferred commercial compositions comprising alpha-amylase include MYCOLASE™ from DSM (Gist Brocades), BAN™, TERMAMYL™ SC, FUNGAMYLT™, LIQUOZYME™ X, LIQUOZYME™ SC and SAN™ SUPER, SAN™ EXTRA L (Novozymes A/S) and CLARASE™ L-40,000, DEX-LO™, SPEZYME™ FRED, SPEZYME™ AA, SPEZYME™ DELTA AA, GC358, GC980, and SPEZYME™ RSL (Danisco A/S), and the acid fungal alpha-amylase sold under the trade name SP288 (available from Novozymes A/S, Denmark).

Carbohydrate-Source Generating Enzyme

The term "carbohydrate-source generating enzyme" includes glucoamylase (a glucose generator), beta-amylase and maltogenic amylase (both maltose generators) and also pullulanase and alpha-glucosidase. A carbohydrate-source generating enzyme is capable of producing a carbohydrate that can be used as an energy-source by the fermenting organism(s) in question, for instance, when used in a process of the invention for producing a fermentation product, such as ethanol. The generated carbohydrate may be converted directly or indirectly to the desired fermentation product, preferably ethanol. According to the invention a mixture of carbohydrate-source generating enzymes may be used. Especially contemplated blends are mixtures comprising at least a glucoamylase and an alpha-amylase, especially an acid amylase, even more preferred an acid fungal alpha-amylase.

The ratio between glucoamylase activity (AGU) and acid fungal alpha-amylase activity (FAU-F) (i.e., AGU per FAU-F) may in a preferred embodiment of the invention be between 0.1 and 100 AGU/FAU-F, in particular between 2 and 50 AGU/FAU-F, such as in the range from 10-40 AGU/FAU-F, especially when doing one-step fermentation (Raw Starch Hydrolysis—RSH), i.e., when saccharification in step (a) and fermentation in step (b) are carried out simultaneously (i.e., without a liquefaction step).

In a conventional starch-to-ethanol process (i.e., including a liquefaction step (a)) the ratio may preferably be as defined in EP 140,410-B1, especially when saccharification and fermentation are carried out simultaneously.

Glucoamylases

A glucoamylase may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al., 1984, *EMBO J.* 3(5): 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Hata et al., 1991, *Agric. Biol. Chem.* 55(4): 941-949), or variants or fragments thereof. Other *Aspergillus* glucoamylase variants include variants with enhanced thermal stability: G137A and G139A (Chen et al., 1996, *Prot. Eng.* 9: 499-505); D257E and D293E/Q (Chen et al., 1995, *Prot. Eng.* 8: 575-582); N182 (Chen et al., 1994, *Biochem. J.* 301: 275-281); disulphide bonds, A246C (Fierobe et al., 1996, *Biochemistry* 35: 8698-8704; and introduction of Pro residues in position A435 and S436 (Li et al., 1997, *Protein Eng.* 10: 1199-1204.

Other glucoamylases include *Athelia rolfsii* (previously denoted *Corticium rolfsii*) glucoamylase (see U.S. Pat. No. 4,727,026 and (Nagasaka et al., 1998, *Appl. Microbiol. Biotechnol.* 50: 323-330), *Talaromyces* glucoamylases, in particular derived from *Talaromyces duponti, Talaromyces emersonii* (WO 99/28448), *Talaromyces leycettanus* (U.S. Pat. No. Re. 32,153), and *Talaromyces thermophilus* (U.S. Pat. No. 4,587,215).

Bacterial glucoamylases include glucoamylases from *Clostridium*, in particular *C. thermoamylolyticum* (EP 135138), and *C. thermohydrosulfuricum* (WO 86/01831), *Trametes cingulata, Pachykytospora papyracea*, and *Leucopaxillus giganteus*, all disclosed in WO 2006/069289; or *Peniophora rufomarginata* disclosed in PCT/US2007/066618; or a mixture thereof. A hybrid glucoamylase may be used in the present invention. Examples of hybrid glucoamylases are disclosed in WO 2005/045018. Specific examples include the hybrid glucoamylase disclosed in Tables 1 and 4 of Example 1 (which hybrids are hereby incorporated by reference).

The glucoamylase may have a high degree of sequence identity to any of above mentioned glucoamylases, i.e., at least 70%, at least 75%, at least 80%, at least 85%, at least 90%, at least 95%, at least 96%, at least 97%, at least 98%, at least 99% or even 100% identity to the mature enzymes sequences mentioned above.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME ULTRA™ and AMG™ E (from Novozymes A/S, Denmark); OPTIDEX™ 300, GC480™ and GC147™ (from Genencor Int., USA); AMIGASE™ and AMIGASE™ PLUS (from DSM); G-ZYME™ G900, G-ZYME™ and G990 ZR (from Genencor Int.).

Glucoamylases may be added in an amount of 0.02-20 AGU/g DS, preferably 0.1-10 AGU/g DS, especially between 0.1-5 AGU/g DS, such as 0.1-2 AGU/g DS, such as 0.5 AGU/g DS or in an amount of 0.0001-20 AGU/g DS, preferably 0.001-10 AGU/g DS, especially between 0.01-5 AGU/g DS, such as 0.1-2 AGU/g DS.

Beta-Amylases

A beta-amylase (E.C 3.2.1.2) is the name traditionally given to exo-acting maltogenic amylases, which catalyze the hydrolysis of 1,4-alpha-glucosidic linkages in amylose, amylopectin and related glucose polymers. Maltose units are successively removed from the non-reducing chain ends in a step-wise manner until the molecule is degraded or, in the case of amylopectin, until a branch point is reached. The maltose released has the beta anomeric configuration, hence the name beta-amylase.

Beta-amylases have been isolated from various plants and microorganisms (Fogarty and Kelly, 1979, *Progress in Industrial Microbiology* 15: 112-115). These beta-amylases are characterized by having a temperature optimum in the range from 40° C. to 65° C. and a pH optimum in the range from 4.5 to 7. A commercially available beta-amylase from barley is NOVOZYM™ WBA from Novozymes A/S, Denmark and SPEZYME™ BBA 1500 from Genencor Int., USA.

Maltogenic Amylases

The amylase may also be a maltogenic alpha-amylase. A "maltogenic alpha-amylase" (glucan 1,4-alpha-maltohydrolase, E.C. 3.2.1.133) is able to hydrolyze amylose and amylopectin to maltose in the alpha-configuration. A maltogenic amylase from *Bacillus stearothermophilus* strain NCIB 11837 is commercially available from Novozymes A/S. Maltogenic alpha-amylases are described in U.S. Pat. Nos. 4,598,048, 4,604,355 and 6,162,628, which are hereby incorporated by reference.

The maltogenic amylase may in a preferred embodiment be added in an amount of 0.05-5 mg total protein/gram DS or 0.05-5 MANU/g DS.

Phytases

Any phytase may be used in a process of the present invention. Phytases are enzymes that degrade phytates and/or phytic acid by specifically hydrolyzing the ester link between inositol and phosphorus. Phytase activity is credited with phosphorus and ion availability in many ingredients. In some embodiments, the phytase is capable of liberating at least one inorganic phosphate from an inositol hexaphosphate (e.g., phytic acid). Phytases can be grouped according to their preference for a specific position of the phosphate ester group on the phytate molecule at which hydrolysis is initiated (e.g., 3-phytase (EC 3.1.3.8) or 6-phytase (EC 3.1.3.26)). An example of phytase is myo-inositol-hexakiphosphate-3-phosphohydrolase.

Phytases can be obtained from microorganisms such as fungal and bacterial organisms. For example, the phytase may be obtained from filamentous fungi such as *Aspergillus* (e.g., *A. ficuum, A. fumigatus, A. niger*, and *A. terreus*), *Cladospirum, Mucor* (e.g., *Mucor piriformis*), *Myceliophthora* (e.g., *M. thermophila*), *Penicillium* (e.g., *P. hordei* (ATCC No. 22053)), *P. piceum* (ATCC No. 10519), or *P. brevi-compactum* (ATCC No. 48944), *Talaromyces* (e.g., *T. thermophilus*), *Thermomyces* (WO 99/49740), and *Trichoderma* spp. (e.g., *T. reesei*).

In an embodiment, the phytate-degrading enzyme is obtained from yeast (e.g., *Arxula adeninivorans, Pichia anomala, Schwanniomyces occidentalis*), gram-negative bacteria (e.g., *Escherichia coli, Klebsiella* spp., *Pseudomonas* spp.), and gram-positive bacteria (e.g., *Bacillus* spp. such as *Bacillus subtilis*).

The phytase also may be obtained from *Citrobacter, Enterbacter*, or *Peniophora*.

In an embodiment, the phytase is derived from *Buttiauxiella* spp. such as *B. agrestis, B. brennerae, B. ferragutiase, B. gaviniae, B. izardii, B. noackiae*, and *B. warmboldiae*. In some embodiments, the phytase is a phytase disclosed in WO 2006/043178 or U.S. application Ser. No. 11/714,487.

In one preferred embodiment, the phytase has at least 75%, at least 80%, at least 85%, at least 88%, at least 90%, at least 93%, at least 95%, at least 96%, at least 97%, at least 98% and at least 99% sequence identity to the amino acid sequence set forth in SEQ ID NO: 31 of U.S. application Ser. No. 12/263,886.

Commercially-available phytases are NATUPHOS (BASF), RONOZYME P (Novozymes A/S), PHZYME (Danisco A/S, Diversa) and FINASE (AB Enzymes). The method for determining microbial phytase activity and the definition of a phytase unit is disclosed in Engelen et al., 1994, *Journal of AOAC International* 77: 760-764. The phytase may be a wild-type phytase, an active variant or active fragment thereof.

Pullulanases

Any pullulanase may be used in a process of the present invention. In an embodiment, the pullulanase is a GH57 pullulanase, e.g., a pullulanase obtained from a strain of *Thermococcus*, including *Thermococcus* sp. AM4, *Thermococcus* sp. HJ21, *Thermococcus barophilus, Thermococcus gammatolerans, Thermococcus hydrothermalis; Thermococcus kodakarensis, Thermococcus litoralis*, and *Thermococcus onnurineus*; or from a strain of *Pyrococcus*, such as *Pyrococcus abyssi* and *Pyrococcus furiosus*.

Proteases

A protease may be added during saccharification, fermentation, simultaneous saccharification and fermentation. The protease may be any protease. In a preferred embodiment the protease is an acid protease of microbial origin, preferably of fungal or bacterial origin. An acid fungal protease is preferred, but also other proteases can be used.

Suitable proteases include microbial proteases, such as fungal and bacterial proteases. Preferred proteases are acidic proteases, i.e., proteases characterized by the ability to hydrolyze proteins under acidic conditions below pH 7.

The acid fungal protease may be derived from *Aspergillus, Candida, Coriolus, Endothia, Enthomophtra, Irpex*, *Mucor, Penicillium, Rhizopus, Sclerotium*, and *Torulopsis*. In particular, the protease may be derived from *Aspergillus aculeatus* (WO 95/02044), *Aspergillus awamori* (Hayashida et al., 1977, *Agric. Biol. Chem.* 42(5), 927-933), *Aspergillus niger* (see, e.g., Koaze et al., 1964, *Agr. Biol. Chem. Japan* 28: 216), *Aspergillus saitoi* (see, e.g., Yoshida, 1954, *J. Agr. Chem. Soc. Japan* 28: 66), or *Aspergillus oryzae*, such as the pepA protease; and acidic proteases from *Mucor miehei* or *Mucor pusillus*.

The protease may be a neutral or alkaline protease, such as a protease derived from a strain of *Bacillus*. A particular protease is derived from *Bacillus amyloliquefaciens* and has the sequence obtainable at Swissprot as Accession No. P06832. The proteases may have at least 90% sequence identity to amino acid sequence obtainable at Swissprot as Accession No. P06832 such as at least 92%, at least 95%, at least 96%, at least 97%, at least 98%, or particularly at least 99% identity.

The protease may have at least 90% sequence identity to the amino acid sequence disclosed as SEQ ID NO: 1 in the WO 2003/048353 such as at 92%, at least 95%, at least 96%, at least 97%, at least 98%, or particularly at least 99% identity.

The protease may be a papain-like protease selected from the group consisting of proteases within E.C. 3.4.22.* (cysteine protease), such as EC 3.4.22.2 (papain), EC 3.4.22.6 (chymopapain), EC 3.4.22.7 (asclepain), EC 3.4.22.14 (actimidain), EC 3.4.22.15 (cathepsin L), EC 3.4.22.25 (glycyl endopeptidase) and EC 3.4.22.30 (caricain).

In an embodiment the protease is a protease preparation derived from a strain of *Aspergillus*, such as *Aspergillus oryzae*. In another embodiment the protease is derived from a strain of *Rhizomucor*, preferably *Rhizomucor miehei*. In another contemplated embodiment the protease is a protease preparation, preferably a mixture of a proteolytic preparation derived from a strain of *Aspergillus*, such as *Aspergillus oryzae*, and a protease derived from a strain of *Rhizomucor*, preferably *Rhizomucor miehei*.

Aspartic acid proteases are described in, for example, Handbook of Proteolytic Enzymes, Edited by A. J. Barrett, N. D. Rawlings and J. F. Woessner, Academic Press, San Diego, 1998, Chapter 270. Suitable examples of aspartic acid protease include, e.g., those disclosed in Berka et al., 1990, *Gene* 96: 313; Berka et al., 1993, *Gene* 125: 195-198; and Gomi et al., 1993, *Biosci. Biotech. Biochem.* 57: 1095-1100, which are hereby incorporated by reference.

Commercially available products include ALCALASE®, ESPERASE™, FLAVOURZYME™, PROMIX™, NEUTRASE®, RENNILASE®, NOVOZYM™ FM 2.0L, and iZyme BA (available from Novozymes A/S, Denmark) and GC106™ and SPEZYME™ FAN from Genencor Int., Inc., USA.

The protease may be present in an amount of 0.0001-1 mg enzyme protein per g DS, preferably 0.001 to 0.1 mg enzyme protein per g DS. Alternatively, the protease may be present in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure, including definitions will be controlling.

Various references are cited herein, the disclosures of which are incorporated by reference in their entireties.

Materials & Methods

Methods:

Identity

The relatedness between two amino acid sequences or between two polynucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two polynucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Glucoamylase Activity

Glucoamylase activity may be measured in Glucoamylase Units (AGU).

Glucoamylase Activity (AGU)

The Novo Glucoamylase Unit (AGU) is defined as the amount of enzyme, which hydrolyzes 1 micromole maltose per minute under the standard conditions 37° C., pH 4.3, substrate: maltose 23.2 mM, buffer: acetate 0.1 M, reaction time 5 minutes.

An autoanalyzer system may be used. Mutarotase is added to the glucose dehydrogenase reagent so that any alpha-D-glucose present is turned into beta-D-glucose. Glucose dehydrogenase reacts specifically with beta-D-glucose in the reaction mentioned above, forming NADH which is determined using a photometer at 340 nm as a measure of the original glucose concentration.

| AMG incubation: | |
|---|---|
| Substrate: | maltose 23.2 mM |
| Buffer: | acetate 0.1M |
| pH: | 4.30 ± 0.05 |
| Incubation temperature: | 37° C. ± 1 |
| Reaction time: | 5 minutes |
| Enzyme working range: | 0.5-4.0 AGU/mL |

| Color reaction: | |
|---|---|
| GlucDH: | 430 U/L |
| Mutarotase: | 9 U/L |
| NAD: | 0.21 mM |
| Buffer: | phosphate 0.12M; 0.15M NaCl |
| pH: | 7.60 ± 0.05 |
| Incubation temperature: | 37° C. ± 1 |
| Reaction time: | 5 minutes |
| Wavelength: | 340 nm |

Alpha-Amylase Activity (KNU)

The alpha-amylase activity may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

One Kilo Novo alpha amylase Unit (KNU) is defined as the amount of enzyme which, under standard conditions (i.e., at 37° C.+/−0.05; 0.0003 M $Ca^{2+}$; and pH 5.6) dextrinizes 5260 mg starch dry substance Merck Amylum solubile.

Acid Alpha-Amylase Activity

When used according to the present invention the activity of an acid alpha-amylase may be measured in AFAU (Acid Fungal Alpha-amylase Units) or FAU-F.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

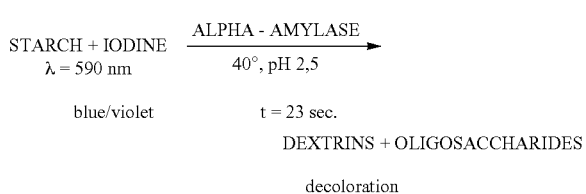

| Standard conditions/reaction conditions: | |
|---|---|
| Substrate: | Soluble starch, approx. 0.17 g/L |
| Buffer: | Citrate, approx. 0.03M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | 590 nm |
| Enzyme concentration: | 0.025 AFAU/mL |
| Enzyme working range: | 0.01-0.04 AFAU/mL |

Determination of FAU-F

FAU-F Fungal Alpha-Amylase Units (Fungamyl) is measured relative to an enzyme standard of a declared strength.

| Reaction conditions | |
| --- | --- |
| Temperature | 37° C. |
| pH | 7.15 |
| Wavelength | 405 nm |
| Reaction time | 5 min |
| Measuring time | 2 min |

Protease Assay Method—AU(RH)

The proteolytic activity may be determined with denatured hemoglobin as substrate. In the Anson-Hemoglobin method for the determination of proteolytic activity denatured hemoglobin is digested, and the undigested hemoglobin is precipitated with trichloroacetic acid (TCA). The amount of TCA soluble product is determined with phenol reagent, which gives a blue color with tyrosine and tryptophan.

One Anson Unit (AU-RH) is defined as the amount of enzyme which under standard conditions (i.e., 25° C., pH 5.5 and 10 minutes reaction time) digests hemoglobin at an initial rate such that there is liberated per minute an amount of TCA soluble product which gives the same color with phenol reagent as one milliequivalent of tyrosine.

The AU(RH) method is described in EAL-SM-0350 and is available from Novozymes A/S Denmark on request.

Protease Assay Method (LAPU)

1 Leucine Amino Peptidase Unit (LAPU) is the amount of enzyme which decomposes 1 microM substrate per minute at the following conditions: 26 mM of L-leucine-p-nitroanilide as substrate, 0.1 M Tris buffer (pH 8.0), 37° C., 10 minutes reaction time.

LAPU is described in EB-SM-0298.02/01 available from Novozymes A/S Denmark on request.

Determination of Maltogenic Amylase Activity (MANU)

One MANU (Maltogenic Amylase Novo Unit) may be defined as the amount of enzyme required to release one micromole of maltose per minute at a concentration of 10 mg of maltotriose (Sigma M 8378) substrate per ml of 0.1 M citrate buffer, pH 5.0 at 37° C. for 30 minutes.

Materials:

Alpha-Amylase A (AA): Hybrid alpha-amylase consisting of *Rhizomucor pusillus* alpha-amylase with *Aspergillus niger* glucoamylase linker and SBD disclosed as V039 in Table 5 in WO 2006/069290 (Novozymes A/S).

Glucoamylase (GA): Glucoamylase derived from *Trametes cingulata* disclosed in SEQ ID NO: 2 in WO 2006/069289 and available from Novozymes A/S.

Yeast: RED START™ available from Red Star/Lesaffre, USA.

EXAMPLES

Example 1

Effect of Pyridoxamine Addition on Ethanol Yield in Fermentation of Liquefied Corn Mash Pyridoxamine (Sigma #P9380) was evaluated for its ability to increase ethanol yields from laboratory-made corn mash when added at the time of liquefaction or at the beginning of fermentation.

Liquefied mashes were made using corn and backset obtained from a commercial ethanol plant in the Midwestern United States (Corn LP, Goldfield, Iowa). All mashes contained 32% Dry Solids (DS) and were liquefied at a pH of 5.8 for 120 minutes in a water bath at 85° C., using the alpha-amylase product Liquozyme SC DS (Novozymes) at a dose of 0.02% w/w of corn. Experimental mashes were treated with pyridoxamine at doses of 10 micrograms/g DS and 50 micrograms/g DS of pyridoxamine in 110 g mash. During liquefaction, the mashes were shaken vigorously every 2 minutes for the first 20 minutes and again at 30 minute intervals until the total liquefaction time equaled 2 hours. All mashes were then frozen overnight.

To each thawed mash, urea was added to a final concentration of 1000 ppm, and penicillin was added to a final concentration of 3 ppm. To test the effects of pyridoxamine in simultaneous saccharification and fermentation (SSF), separate aliquots of liquefied mash were dosed with 10 micrograms/g DS and 50 micrograms/g DS of pyridoxamine, respectively. The mashes were fermented as follows:

For fermentation, between 4 and 5 grams of each mash was added to 6 pre-weighed tubes per treatment. Each tube had a hole drilled into its lid to allow for $CO_2$ release. One hundred microliters of Fermentis Red Star yeast (5.5 g yeast in 100 mL tap water incubated at 32° C. for 30 minutes) was added to each tube, and the gluocoamylase product Spirizyme Ultra™ (Novozymes) was added to each tube to achieve a dose of 0.5 AGU/g DS.

After 24 hours, one replicate from each mash was sacrificed for HPLC analysis using 50 microliters of 40% v/v $H_2SO_4$. The tubes were centrifuged at 1500×g for 10 minutes, and the supernatants were filtered using Whatman syringe filters with 0.45 micron membranes, then diluted 1:5 for HPLC analysis. The remaining samples were sacrificed after 54 hours in the same manner but were subjected to HPLC analysis without dilution. Ethanol and oligosaccharide concentrations were measured by HPLC using an HPX-87H column (Bio-Rad) heated to 65° C. with a mobile phase of 5 mM sulfuric acid at a flow rate of 0.6 ml/min, with refractive index detection at 50° C.

Results from two separate experiments are shown in the tables below.

| Treatment | Dose | Addition Point | EtOH, w/v % | *Level |
| --- | --- | --- | --- | --- |
| Control | 0 | | 11.86 | B |
| Pyridoxamine | 10 | Liq | 12.19 | A |
| Pyridoxamine | 50 | Liq | 12.23 | A |
| Pyridoxamine | 10 | SSF | 11.89 | B |
| Pyridoxamine | 50 | SSF | 11.79 | B |

| Treatment | Dose | Addition Point | EtOH, w/v % | *Level |
| --- | --- | --- | --- | --- |
| Control | 0 | | 11.84 | B |
| Pyridoxamine | 10 | Liq | 12.01 | A |
| Pyridoxamine | 50 | Liq | 11.86 | B |
| Pyridoxamine | 10 | SSF | 11.75 | C |
| Pyridoxamine | 50 | SSF | 11.75 | C |

*Levels indicate statistical significance: Results within an experiment sharing a letter are not statistically different from one another.

Three of the four results (both doses of 10 micrograms/g DS and one dose of 50 micrograms/g DS pyridoxamine) demonstrate that the addition of pyridoxamine at the start of corn mash liquefaction resulted in a statistically significant increase in ethanol yield. Addition of pyridoxamine at the beginning of SSF (after liquefaction) did not result in an increase in ethanol yield.

The invention is described in the following paragraphs:

[1]. A process of producing a fermentation product, comprising:

(a) liquefying a starch-containing material to a dextrin with an alpha-amylase in the presence of pyridoxamine;
(b) saccharifying the dextrin to a sugar with a saccharifying enzyme; and
(c) fermenting the sugar using a fermenting organism.

[2]. A process of producing a fermentation product, comprising:
(a) treating a starch-containing material with an alpha-amylase in the presence of pyridoxamine;
(b) liquefying the treated starch-containing material to a dextrin with an alpha-amylase;
(c) saccharifying the dextrin to a sugar with a saccharifying enzyme; and
(d) fermenting the sugar using a fermenting organism to produce the fermentation product.

[3]. A process of producing a sugar, comprising:
(a) liquefying a starch-containing material to a dextrin with an alpha-amylase in the presence of pyridoxamine; and
(b) saccharifying the dextrin to a sugar with a saccharifying enzyme.

[4]. A process of producing a sugar, comprising:
(a) treating a starch-containing material with an alpha-amylase in the presence of pyridoxamine;
(b) liquefying the treated starch-containing material to a dextrin with an alpha-amylase; and
(c) saccharifying the dextrin to a sugar with a saccharifying enzyme.

[5]. The process of paragraph [3] or [4], wherein the sugar is maltose.

[6]. The process of paragraph [3] or [4], wherein the sugar is glucose.

[7]. The process of paragraph [6], further comprising converting glucose to fructose.

[8]. The process of any of paragraphs [3]-[6], further comprising recovering the sugar.

[9]. The process of any of paragraphs [3], [4], [6] and [7], further comprising recovering the fructose.

[10]. A process of producing a dextrin, comprising
(a) liquefying a starch-containing material to the dextrin with an alpha-amylase in the presence of pyridoxamine.

[11]. A process of producing a dextrin, comprising:
(a) treating a starch-containing material with an alpha-amylase in the presence of pyridoxamine; and
(b) liquefying the treated starch-containing material to a dextrin with an alpha-amylase.

[12]. The process of paragraph [10] or [11], further comprising recovering the dextrin.

[13]. The process of any of paragraphs [1]-[12], wherein the pyridoxamine is present in an amount of 1-100 micrograms/g dry solids, e.g., 5-50, 10-40, 10-25 micrograms/g dry solids.

[14]. The process of any of paragraphs [2], [4], [5], [6], [7], [8], [9], [11], [12], and [13], wherein the starch-containing material is treated with an alpha-amylase at a temperature of 20-75° C., e.g., 25-65° C. or 40-60° C.

[15]. The process of any of paragraphs [1]-[14], wherein the starch-containing material or the treated liquefied starch-containing material is liquefied to a dextrin at a temperature of 65-110° C., e.g., 80-100° C. or 80-90° C.

[16]. The process of any of paragraphs [1]-[15], wherein the liquefaction comprises jet-cooking at a temperature between 95-140° C.

[17]. The process of any of paragraphs [1]-[16], wherein the liquefaction is performed in the presence of a phytase, a pullulanase and/or an isoamylase.

[18]. The process of any of paragraphs [1]-[9] and [13]-[17], wherein the saccharifying enzyme is a beta-amylase, glucoamylase, or maltogenic alpha-amylase.

[19]. The process of any of paragraphs [1]-[9] and [13]-[18], wherein the saccharification and/or the fermentation are performed in the presence of a protease.

[20]. The process of any of paragraphs [1]-[9] and [13]-[19], wherein the saccharification is carried out at a temperature in the range of 20-75° C.

[21]. The process of any of paragraphs [1]-[9] and [13]-[20], further comprising a pre-saccharification prior to saccharification.

[22]. The process of paragraph [21], wherein the pre-saccharification is performed for 40-90 minutes at a temperature between 30-65° C.

[23]. The process of any of paragraphs [1]-[3] and [13]-[22], wherein the saccharification and fermentation are performed simultaneously.

[24]. The process of paragraph [23], wherein the saccharification and fermentation are carried out at a temperature in the range of 20° C. to 40° C.

[25]. The process of any of paragraphs [1]-[3] and [13]-[24], wherein the fermenting organism is a yeast.

[26]. The process of any of paragraphs [1]-[25], wherein the starch-containing material is selected from the group consisting of barley, beans, cassaya, cereals, corn, milo, peas, potatoes, rice, rye, sago, sorghum, sweet potatoes, tapioca, wheat, and whole grains, or any mixture thereof.

[27]. The process of any of paragraphs [1], [2], and [13]-[26], wherein the fermentation product is selected from the group consisting of alcohols (e.g., ethanol, methanol, butanol, 1,3-propanediol); organic acids (e.g., citric acid, acetic acid, itaconic acid, lactic acid, gluconic acid, gluconate, lactic acid, succinic acid, 2,5-diketo-D-gluconic acid); ketones (e.g., acetone); amino acids (e.g., glutamic acid); gases (e.g., $H_2$ and $CO_2$), and more complex compounds, including, for example, antibiotics (e.g., penicillin and tetracycline); enzymes; vitamins (e.g., riboflavin, $B_{12}$, beta-carotene); and hormones.

[28]. The process of paragraph [27], wherein the fermentation product is ethanol.

[29]. The process of any of paragraphs [1], [2], and [13]-[28], further comprising recovering the fermentation product.

[30]. The process of paragraph [29], wherein the fermentation product is recovered by distillation.

The invention claimed is:

1. A process of producing a fermentation product, comprising:
   (a) liquefying a starch-containing material to a dextrin at 60-95° C. with an alpha-amylase in the presence of a vitamin consisting of pyridoxamine;
   (b) saccharifying the dextrin to a sugar with a saccharifying enzyme; and
   (c) fermenting the sugar in the presence of a yeast, thereby producing the fermentation product.

2. A process of producing a fermentation product, comprising:
   (a) treating a starch-containing material with an alpha-amylase in the presence of a vitamin consisting of pyridoxamine;
   (b) liquefying the treated starch-containing material to a dextrin at 60-95° C. with an alpha-amylase;
   (c) saccharifying the dextrin to a sugar with a saccharifying enzyme; and
   (d) fermenting the sugar in the presence of a yeast, thereby producing the fermentation product.

3. A process of claim 1, wherein the fermentation product is ethanol.

4. A process of claim 2, wherein the fermentation product is ethanol.

5. The process of claim 1, wherein the pyridoxamine is present in an amount of 1-100 micrograms/g dry solids.

6. The process of claim 1, wherein the step liquefying is performed in the presence of a phytase, a pullulanase and/or an isoamylase.

7. The process of claim 1, wherein the saccharifying enzyme is a beta-amylase, glucoamylase, or maltogenic alpha-amylase.

8. The process of claim 1, wherein the saccharification and/or the fermentation are performed in the presence of a protease.

9. The process of claim 1, wherein the saccharification is carried out at a temperature in the range of 20-75° C.

10. The process of claim 1, further comprising a pre-saccharification prior to saccharification.

11. The process of claim 1, wherein the saccharification and fermentation are performed simultaneously.

12. The process of claim 1, wherein the fermentation product is selected from the group consisting of alcohols, organic acids, ketones, amino acids, gases, antibiotics, enzymes, vitamins, and hormones.

13. The process of claim 1, wherein the pyridoxamine is present in an amount of 5-50 micrograms/g dry solids.

14. The process of claim 1, wherein the pyridoxmine is present in an amount of 10- 40 micrograms/g dry solids.

15. The process of claim 1, wherein the pyridoxmine is present in an amount of 10-25 micrograms/g dry solids.

16. The process of claim 1, wherein the step of liquefying is at a temperature of 80-90° C.

17. The process of claim 2, wherein the pyridoxamine is present in an amount of 1-100 micrograms/g dry solids.

18. The process of claim 2, wherein the step of liquefying is performed in the presence of a phytase, a pullulanase and/or an isoamylase.

19. The process of claim 2, wherein the saccharifying enzyme is a beta-amylase, glucoamylase, or maltogenic alpha-amylase.

20. The process of claim 2, wherein the saccharification and/or the fermentation are performed in the presence of a protease.

21. The process of claim 2, wherein the saccharification is carried out at a temperature in the range of 20-75° C.

22. The process of claim 2, further comprising a pre-saccharification prior to saccharification.

23. The process of claim 2, wherein the saccharification and fermentation are performed simultaneously.

24. The process of claim 2, wherein the fermentation product is selected from the group consisting of alcohols, organic acids, ketones, amino acids, gases, antibiotics, enzymes, vitamins, and hormones.

25. The process of claim 2, wherein the pyridoxamine is present in an amount of 5-50 micrograms/g dry solids.

26. The process of claim 2, wherein the pyridoxamine is present in an amount of 10-40 micrograms/g dry solids.

27. The process of claim 2, wherein the pyridoxamine is present in an amount of 10-25 micrograms/g dry solids.

28. The process of claim 2, wherein the step of liquefying is at a temperature of 80-90° C.

\* \* \* \* \*